(12) United States Patent
Dillon

(10) Patent No.: US 8,084,051 B1
(45) Date of Patent: *Dec. 27, 2011

(54) THERAPEUTIC MEDICAL GARMENTS WITH SILICONE SHEETING COMPONENT FOR SCAR TREATMENT, PROCESS OF MANUFACTURE AND USE

(75) Inventor: Mark E. Dillon, Allentown, PA (US)

(73) Assignee: Bio Med Sciences, Inc., Allentown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/554,993

(22) Filed: Nov. 13, 1995

(51) Int. Cl.
- *A01N 25/34* (2006.01)
- *A61F 13/00* (2006.01)
- *A61F 5/44* (2006.01)
- *A61B 5/04* (2006.01)

(52) U.S. Cl. ........ 424/402; 424/442; 604/345; 600/388; 600/389; 600/391

(58) Field of Classification Search .......... 424/402, 424/449, 422, 443–445; 604/345; 600/388, 600/389, 391; 427/387
See application file for complete search history.

(56) References Cited

U.S. PATENT DOCUMENTS

| | | | | |
|---|---|---|---|---|
| 3,434,875 A | * | 3/1969 | Hinton, Jr. et al. | 442/104 |
| 4,044,404 A | * | 8/1977 | Martin et al. | 623/1.54 |
| 4,355,600 A | * | 10/1982 | Zielinski | 119/850 |
| 4,630,610 A | * | 12/1986 | Fletcher | 128/501 |
| 4,701,964 A | * | 10/1987 | Bell et al. | 2/406 |
| 4,832,009 A | * | 5/1989 | Dillon | 128/156 |
| 5,137,508 A | * | 8/1992 | Engman | 602/79 |
| 5,158,541 A | * | 10/1992 | McCurley | 602/79 |
| 5,306,503 A | * | 4/1994 | Muller et al. | 424/449 |
| 5,656,279 A | * | 8/1997 | Dillon | 424/402 |

OTHER PUBLICATIONS

Dillion, ME, Silicone and Poly(Tetrafluoroethylene) Interpenetrating Polymer, Nov. 1992.*
Dillon, "Silicone and Poly(tetrafluoroethylene) Interpenetrating Polymer Networks" American Chemical Society, p. 394-404.*
"Topical silicone gel: a new treatment for hypertrophic scars" by Ahn et al., surgery Oct. 1989; 106(4):781-6.*
"Silicone gel sheeting in scar therapy" by Katz, Cutis. Jul. 1995; 56(1): 65-7.*
"Topical silicone gel sheeting in the treatment of hypertrophic scars and keloids. A dermatologic experience" by Gold, J Dermatol Sur Oncol. Oct. 1993; 19(10): 912-6.*

* cited by examiner

*Primary Examiner* — Isis Ghali
(74) *Attorney, Agent, or Firm* — John F. A. Earley, III; Frank J. Bonini, Jr.; Harding, Earley, Follmer & Frailey, P.C.

(57) ABSTRACT

Therapeutic medical garments for scar treatment includes a composite fabric for treating dermatological scars, wherein a layer of textile fabric and a layer of a therapeutic agent produce a composite sheet suitable for the treatment of dermatologic scars resulting from traumatic, surgical or other injuries to the skin. The composite sheet may be fashioned into garments fitted to the patient for convenience of use, optimization of skin contact, and single step application of pressure therapy and the therapeutic agent. A process of use of the medical garment for applying therapeutic agent and pressure therapies.

14 Claims, 1 Drawing Sheet

THERAPEUTIC MEDICAL GARMENTS WITH SILICONE SHEETING COMPONENT FOR SCAR TREATMENT, PROCESS OF MANUFACTURE AND USE

BACKGROUND OF THE INVENTION

1. Field of the Invention

This invention relates to therapeutic medical garments for the treatment of scars, and more specifically for the prevention or management of hypertrophic scars and keloids.

2. Description of the Prior Art

Therapeutic medical binder garments have been used for many years to apply pressure to anatomic regions after surgical procedures such as reduction mammaplasties, abdominoplasties, and rhytidectomies (face-lifts). Similar pressure application garments have become a standard of care in the management of hypertrophic scars and keloids subsequent to burn injuries.

As disclosed in my co-pending patent application Ser. No. 08/200,152 filed Feb. 23, 1994, silicone elastomer materials are also used in the medical field for the management of dermal scarring which often results from burns, traumatic injuries, or surgical incisions. These silicone materials soften scar tissue and improve the cosmetic as well as functional aspects of such scars over a period of weeks and months. The biological mechanism for this effect is poorly understood. It is, however, known that the therapeutic benefit is derived independently of pressure applied to the scar surface.

It is common practice in the scar management field to combine pressure therapy with silicone sheeting in highly critical areas such as the hands or face, or other areas of aesthetic, importance. In this fashion, a maximum effect can be achieved in a minimum amount of time.

Difficulties arise in placing silicone sheeting materials under textile garments over complex contours of the body. These difficulties primarily relate to an inability to avoid wrinkles and folds in the silicone elastomer, patient compliance with the tedious application on a daily basis, positioning and maintenance of the sheet during movement, and providing optimal skin contact.

My co-pending patent application Ser. No. 08/200,152 discloses an interpenetrating polymer network (IPN) of silicone and polytetrafluoroethylene (PTFE) which has improved physical properties while having decreased thickness. While it is possible to apply the IPN material over complex anatomical contours under pressure application devices without folds or gaps, it is still a tedious task and maintaining position remains difficult.

For the purpose of this invention, the terms silicone elastomer, silicone gel, or silicone IPN will be equivalent and used interchangeably, since it is believed that this invention may be accomplished with any of these materials.

SUMMARY OF THE INVENTION

This invention relates to scar treatment and more particularly to a composite structure for scar treatment which incorporates the convenience and simplicity of donning garments. Further, this invention relates to composite structures which incorporate the pressure therapy features of therapeutic medical binder garments with the use of silicone elastomers for scar management.

By applying a surface layer of silicone elastomeric material to one side of a suitable textile fabric prior to garment fabrication, I have unexpectedly discovered that shaped garments may be produced which provide a surface layer of silicone for uniform skin contact even when shaped into complex geometric forms. The finished product is easily donned and maintains the position of the silicone sheeting material with respect to the application site. In addition, the material is durable and capable of being machine washed and dried.

The therapeutic medical garments of this invention are made of a soft silicone elastomer layer bonded to a textile fabric layer, and the silicone elastomer layer is placed in contact with the patient's skin.

The manufacturing process lends itself to large-scale production in that flat sheets are produced for final shape-forming by traditional garment manufacturing processes. This provides for rapid and cost effective production of ready-to-wear or custom made shapes for any given patient.

This invention is an improvement over the prior art in that (a) the silicone layer is bonded to the surface of an elastic textile fabric to produce a therapeutic medical garment, (b) the medical garment is easily donned without creating folds or gaps between the silicone layer and the skin, (c) both pressure and silicone therapies may be applied concomitantly without requiring a separate and/or repeated process of fitting both materials to the skin individually, and (d) patient compliance may be improved because daily application of the therapy is greatly facilitated.

DETAILED DESCRIPTION OF SEVERAL EMBODIMENTS

Figure 1:
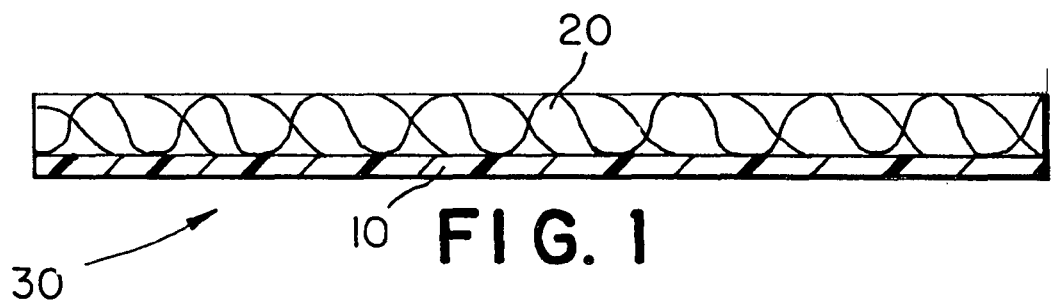
FIG. 1 is a schematic diagram of one embodiment of this invention wherein a silicone elastomer layer 10 is bonded to an elastic textile fabric layer 20 to form a composite fabric 30.
Figure 2:
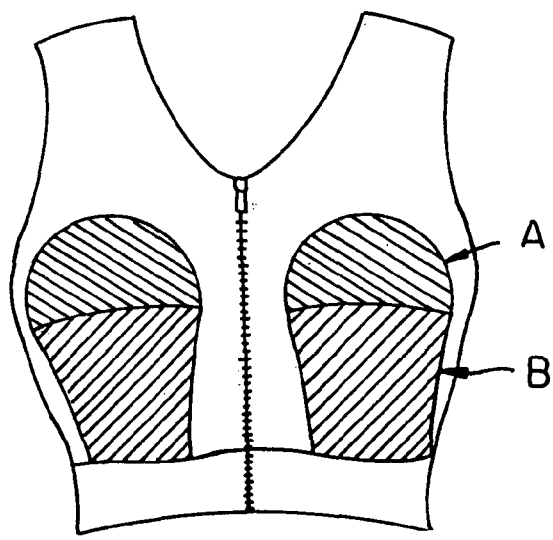
FIG. 2 is a plan view of a therapeutic medical garment with regions (A) and (B) constructed of the composite layer formed by the silicone and textile layers of this invention.

A preferred embodiment of this invention is shown in the following illustrative examples and is not intended to be limiting.

There are many silicone compositions that are suitable for use in this invention either in combination or in blends. In addition current clinical investigations indicate that other materials, such as hydrogels or hydrocolloids, may be similarly effective for scar reduction and therefore also useful for this invention. However, hydrogels or hydrocolloids in general, such as silicone copolymers containing mineral oil, lack sufficient durability to provide reasonably economical use in the garment which must last for months.

There are numerous textile fabric materials which may be useful for the purpose of this invention. Furthermore, various thicknesses of textile fabric layers and layers of therapeutic agent may be useful, and components of various elasticities could be used. For example, the textile fabric layer may be comprised of a blend of 89% nylon and 11% Spandex. The primary consideration is that the medical garment of this invention has suitable tactile qualities that make it comfortable for the patient to wear, applies pressure that is suitable, and has an efficacious therapeutic agent which is applies to the skin where needed. It is also important that the finished product is capable of being washed by ordinary methods, and that the product has sufficient durability to allow repeated use and cost effectiveness.

Example 1

My U.S. patent application Ser. No. 08/200,152, discloses a method of manufacturing a simultaneous interpenetrating polymer network (IPN) of silicone and polytetrafluoroethylene (PTFE). The process involves using a release liner as a carrier substrate onto which the elastomer sheeting is formed. The substrate is passed through a coating station which deposits a layer of the uncured silicone/PTFE mixture. The carrier is then passed through a tunnel style oven to vulcanize the silicone.

The silicone layer was tightly bound to the textile fabric and could not be removed from its surface using mechanical techniques. Samples of fabric were washed and dried using an ordinary household washing machine and drier 5 (five) times according to Military Specification-44187B test method 4.5.5. without signs of delamination or wear.

A commercially available brassiere from Playtex Apparel, Inc. was purchased from a retail outlet. The cup panels of the garment were removed and replaced with the silicone textile composite material of this invention such that the silicone surface of the composite textile material faced inward to provide contact with the patient's skin. The resulting product was a single piece garment suitable for scar reduction therapy of, for example, reduction mammaplasty incisions.

In this example, a commercially available brassiere was remodeled to use the composite layers of this invention. It is obvious that a garment may be initially manufactured with fabric panels comprised of the composite layers of this invention. An ordinary cutting pattern may be utilized, with the silicone textile composite layer used for the appropriate panel cuts and ordinary fabric used for the remainder. In addition, a variety of brassiere designs would be suitable for similar use.

Numerous other types of therapeutic medical garments may be produced by the process disclosed above. Other similar articles include abdominoplasty garments, facial slings for rhytidectomy procedures, and the like. In addition, various forms of therapeutic medical binders used for burn scar management may likewise be produced, such as gloves, facemasks, vests, etc. Garments of a less compressive design are also useful to promote comfort and use beyond the period where the function of a binder garment is desired. Furthermore, it is contemplated that the finished product may be supplied in sheets for custom tailoring by a clinician.

The invention claimed is:

1. A composite material for use in the construction of therapeutic medical garments worn by a patient to treat dermatological scars comprising:
    means for treating dermatological scars comprising a therapeutic layer having scar treatment properties constructed and arranged to contact the skin of a patient for a duration time which the patient wears the therapeutic medical garment, the therapeutic layer being a therapeutic agent for the treatment of dermatological scars comprising a therapeutic agent selected from the group consisting of silicone gel, silicone elastomer and silicone interpenetrating polymer network, and a backing layer of a textile fabric bonded to the therapeutic layer, wherein the backing layer is a component of the garment.

2. The composite material of claim 1, wherein the fabric of the second backing layer is a textile comprised of a blend of 89% nylon fibers and 11% Spandex elastic textile fibers.

3. A composite material for therapeutic medical garments for the treatment of dermatologic scars of a patient, comprising a first layer of a therapeutic agent bonded to a second backing layer of a textile fabric formed into garments with the first layer being placed in contact with the skin of the patient, wherein the therapeutic agent is selected from the group consisting of silicone gel, silicone elastomer and silicone interpenetrating polymer network and the fabric of the second backing layer is a textile fabric comprised of a blend of 89% nylon fibers and 11% Spandex elastic fibers.

4. A therapeutic medical garment worn by a patient for treating dermatological scars, said garment being suitable for donning and capable of being machine washed and dried, at least one section of said garment comprising:
    a composite material used in the construction of said garment, the composite material including means for treating dermatological scars comprising a therapeutic layer having scar treatment properties constructed and arranged to contact the skin of a patient for a duration of time which the patient wears the therapeutic medical garment, said therapeutic layer being selected from the group consisting of silicone gel, silicone elastomer and silicone interpenetrating polymer network, and
    a backing layer of a textile fabric bonded to the therapeutic layer,
    said garment holding said therapeutic layer in contact with the skin of the patient without adhesion to the skin.

5. The article of claim 4, wherein the textile fabric is a blend of 89% nylon fibers and 11% Spandex elastic fibers.

6. The article of claim 4, wherein the therapeutic agent is an interpenetrating polymer network of silicone and polytetrafluoroethylene which is bonded to a second layer of textile fabric, and the textile fabric is a blend of 89% nylon and 11% Spandex elastic fibers.

7. The article of claim 4, wherein the garment is fashioned as a brassiere.

8. A process of producing a composite therapeutic medical garment for the treatment of dermatologic scars, comprising passing a sheet of elastic textile fabric through a coating apparatus, and depositing onto said textile fabric a surface layer of a therapeutic agent selected from the group consisting of silicone gel, silicone elastomer and silicone interpenetrating polymer network, and
    fabricating a garment from said coated textile fabric.

9. The process of claim 8, wherein the textile fabric is comprised of a blend of 89% nylon and 11% Spandex elastic fibers.

10. A process of using a therapeutic medical garment for scar treatment, comprising the steps of: passing a sheet of textile fabric through a coating apparatus, said fabric having a controlled elastic stretch, depositing a sheet of a therapeutic agent selected from the group consisting of silicone gel, silicone elastomer and silicone interpenetrating polymer network, onto the textile fabric to form a composite sheet of a therapeutic layer and a stretchable layer, fabricating a therapeutic medical garment from the composite sheet that is fitted to the patient and is comfortable to wear,
    placing the therapeutic medical garment on the patient with the therapeutic layer facing the patient, contacting the skin of the patient with the therapeutic agent from the therapeutic layer, and elastically holding the therapeutic layer onto the skin of the patient by the elastically stretchable layer to exert pressure therapy on the patient as well as the therapeutic agent therapy.

11. A process of using a therapeutic medical garment for scar treatment, comprising the steps of: passing a sheet of textile fabric through a coating apparatus, said fabric having a controlled elastic stretch, depositing a sheet of therapeutic agent selected from the group consisting of silicone gel, silicone elastomer and silicone interpenetrating polymer network onto the textile fabric to form a composite sheet of a therapeutic medical garment from the composite sheet that is fitted to the patient and in comfortable to wear,
    placing the therapeutic medical garment on the patient with the therapeutic layer facing the patent, contacting the skin of the patient with the therapeutic agent form the therapeutic layer, and elastically holding the therapeutic layer onto the skin of the patient by the elastically stretchable layer to exert pressure therapy on the patient as well as the therapeutic agent therapy.

12. A process of treating dermatological scars of a patient, comprising providing a therapeutic medical garment for treating dermatological scars, said garment being suitable for donning and capable of being machine washed and dried, at least one section of said garment comprising a composite material used in the construction of the garment said composite material including means for treating dermatological scars comprising a therapeutic layer having scar treatment properties constructed and arranged to contact the skin of a patient during the time when the patient wears the garment to therapeutically treat dermatological scars in contact therewith, the therapeutic agent being selected from the group consisting of silicone gel, silicone elastomer and silicone interpenetrating polymer network, and said composite material also comprising a backing layer of textile fabric bonded to the therapeutic layer,
    placing the therapeutic medical garment on a patient with the therapeutic layer facing the patient, and
    contacting the therapeutic layer to a scar site on the skin of the patient during the time when the patient wears the garment to apply therapeutic agent therapy at the scar site.

13. A composite material for use in the construction of therapeutic medical garments worn by a patient as part of the patient's garments to treat dermatological scars of the patient, comprising means for treating dermatological scars comprising a therapeutic layer having scar treatment properties constructed and arranged to contact the skin of a patient for a duration time which the patient wears the therapeutic medical garment to therapeutically treat dermatological scars in contact therewith, the therapeutic layer being selected from the group consisting of silicone gel, silicone elastomer and silicone interpenetrating polymer network, and being a therapeutic agent for the treatment of dermatological scars, and a backing layer of a textile fabric bonded to the therapeutic layer.

14. A process of treating dermatological scars of a patient, comprising providing a therapeutic medical garment for treating dermatological scars, said garment being suitable for donning and capable of being machine washed and dried, at least one section of said garment, comprising a composite material used in the construction of the garment, said composite material including means for treating dermatological scars comprising a therapeutic layer comprising a compound containing silicon and having scar treatment properties constructed and arranged to contact the skin of a patient during the time when the patient wears the garment to therapeutically treat dermatological scars in contact therewith, the therapeutic layer comprising a therapeutic agent for the treatment of dermatological scars, the therapeutic agent being selected from the group consisting of silicone gel, silicone elastomer and silicone interpenetrating polymer network, said composite material also comprising a backing layer of textile fabric bonded to the therapeutic layer,
    placing the therapeutic medical garment on a patient with the therapeutic layer facing the patient, and
    contacting the therapeutic layer to a scar site on the skin of the patient during the time when the patient wears the garment to apply therapeutic agent therapy at the scar site.

* * * * *